(12) United States Patent
Kosaka

(10) Patent No.: US 8,796,014 B2
(45) Date of Patent: Aug. 5, 2014

(54) METHOD FOR PRODUCING TISSUE CELLS FROM PLURIPOTENT STEM CELLS DERIVED FROM IRIS PIGMENT EPITHELIAL CELLS OF ANIMAL AND TISSUE CELL OBTAINED BY METHOD

(75) Inventor: Mitsuko Kosaka, Okayama (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 1080 days.

(21) Appl. No.: 10/559,783

(22) PCT Filed: Jun. 10, 2004

(86) PCT No.: PCT/JP2004/008120
§ 371 (c)(1),
(2), (4) Date: Dec. 8, 2005

(87) PCT Pub. No.: WO2004/111212
PCT Pub. Date: Dec. 23, 2004

(65) Prior Publication Data
US 2006/0141621 A1    Jun. 29, 2006

(30) Foreign Application Priority Data
Jun. 11, 2003  (JP) .................................. 2003-166684

(51) Int. Cl.
*C12N 5/00*    (2006.01)
*G01N 33/53*   (2006.01)
*C12N 5/071*   (2010.01)
*C12Q 1/68*    (2006.01)

(52) U.S. Cl.
USPC ............ 435/325; 435/7.1; 435/6.11; 435/377

(58) Field of Classification Search
None
See application file for complete search history.

(56) References Cited

U.S. PATENT DOCUMENTS 6,500,668 B2 * 12/2002 Samarut et al. ................ 435/383

FOREIGN PATENT DOCUMENTS

JP         3723-152 B2       9/2005

OTHER PUBLICATIONS

Tsonis P.A. Differentiation 70: 397-409, 2002.*
Tsonis, P. Differentiation 70: 397-409, 2002.*
Kirschstein, R. and Skirboll, LR, Stem Cells, NIH, Chapter 3, pp. 1-11, front and back cover, Jun. 2001.*
Friel et al. Adv Drug Del Rev 57: 1894-1903, 2005.*
Hawley and Sobieski, Stem Cells 20: 195-197, 2002.*
Rezai et al., Invest Opthalmol Vis Sci 38:2255-2260, 1997.*
Weiss et al. PNAS 83: 2238-2242, 1986.*
Mokry et al. Acta Med 50: 35-41, 2007.*
Pardo et al. (Brain Res 818: 84-95, 1999).*
N2 Product Description Sheet from Stem Cell technologies (Oct. 2002)—2 pages.*
Lee et al Theriogenology 44: 71-83, 1995.*
Kitchens et al. J. Neurobiol 25: 797-807, 1994—abstract.*
Link et al (Dev Biol 203: 163-176, 1998).*
Pachernik et al (Reprod Nutr Dev 42: 317-326, 2002).*
Inoue et al (ARVO Ann Meet Abstract Search Prog Planner, 2003: Abstract No. 1692, 2003).*
Zhao, Shulei, et al., "In vitro transdifferentiation of embryonic rat retinal pigment epithelium to neural retina," Brain Research 677 (1995), pp. 300-310.
Layer, Paul G., et al., "Pigmented epithelium sustains cell proliferation and decreases expression of opsins and acetylcholinesterase in reaggregated chicken retinospheroids," European Journal of Neuroscience, vol. 9: (1997) pp. 1795-1803.
Korean Office Action for Korean Patent Application No. 10-2005-7023771 and English language translation thereof.
Supplementary European Search Report dated Jun. 9, 2006 for Application No. 04745750.2 corresponding to PCT/JP2004008120.
Paquet-Durand, François et al., Turning teratocarcinoma cells into neurons: rapid differentiation of NT-2 cells in floating spheres, Developmental Brain Research 142 (2003) 161-167, Feb. 26, 2003.
Hu, Dan-Ning et al., "Isolation and Cultivation of Human Iris Pigment Epithelium," Investigative Ophthalmology & Visual Science, vol. 33, No. 8, Jul. 1992.
Haruta, Masatoshi et al., "Induction of Photoreceptor-Specific Phenotypes in Adult Mammalian Iris Tissue", Nature Neuroscience, vol. 4 No. 12, Dec. 2001, pp. 1163-1164.
Reynolds, Brent A. and Weiss, Samuel, "Generation of Neurons and Astrocytes from Isolated Cells of the Adult Mammalian Central Nervous System", Science, vol. 255, Mar. 27, 1992, pp. 1707-1710.
Hayashi T. et al., Regulated Lens Regeneration from Isolated Pigmented Epithelial Cells of Newt Iris in Culture in Response to FGF2/4, Differentiation, 2002, vol. 70, Nos. 2 to 3; pp. 101-108.
Kosaka, M. et al., "In Vitro Culture System for Iris-Pigmented Epitherial Cells for Molecular Analysis of Transdifferentiation", Ex. Cell. Res., 1998, vol. 245, pp. 245-251.

(Continued)

*Primary Examiner* — Daniel E Kolker
*Assistant Examiner* — Aditi Dutt
(74) *Attorney, Agent, or Firm* — Edwards Wildman Palmer LLP; David G. Conlin; Lisa Swiszcz

(57) ABSTRACT

A method for producing tissue cells derived from iris pigmented epithelial cells of an animal, and tissue cells obtained by the method are provided. The method and the tissue cells solve problems such as immunological rejection in cell transplantation, ethical issues, and unbalance between the demand and supply of transplant cell sources.

In the method of the present invention for producing the tissue cells, first, the iris pigmented epithelial cells isolated from an eyeball of an animal are selectively cultured according to a floated coagulated mass culturing technique so as to obtain pluripotent stem cells. Thereafter, the pluripotent stem cells are cultured by using, for example, serum so as to produce various tissue cells.

11 Claims, 5 Drawing Sheets

(56) References Cited

OTHER PUBLICATIONS

Tomita, H. et al., "Momaku Soshiki Saisei Chiryo eno Approach" (Approach for Treatment of Retinal Degenerative Diseases), Drug Delivery System, Mar. 20, 2003, vol. 18, No. 2, pp. 95-103 (in Japanese with English Abstract).

International Search Report dated Jul. 20, 2004 for corresponding Application No. PCT/JP2004/008120 (in English and Japanese). (2 pages).

Japanese Office Action issued in JP 2005-506918, Jul. 8, 2008.

Proceedings of 33$^{rd}$ Meeting of the Japanese Society of Developmental Biologists (2000), vol. 33, p. 6 (SB04).

Proceedings of 36$^{th}$ Meeting of the Japanese Society of Developmental Biologists (received by JST on Jun. 10, 2003) vol. 36, p. 38 (SII-3).

Proceedings of 36$^{th}$ Meeting of the Japanese Society of Developmental Biologists (received by JST on Jun. 10, 2003) vol. 36, p. 210 (1P116).

Tropepe et al., "Retinal Stem Cells in the Adult Mammalian Eye," Science, 2000, vol. 287, p. 2032-2036.

Ahmad et al., "Identification of Neural IProgenitors in the Adult Mammalilan Eye," Biochem. Biophys. Res. Commun. (2000) vol. 270, p. 517-521.

\* cited by examiner

FIG. 2
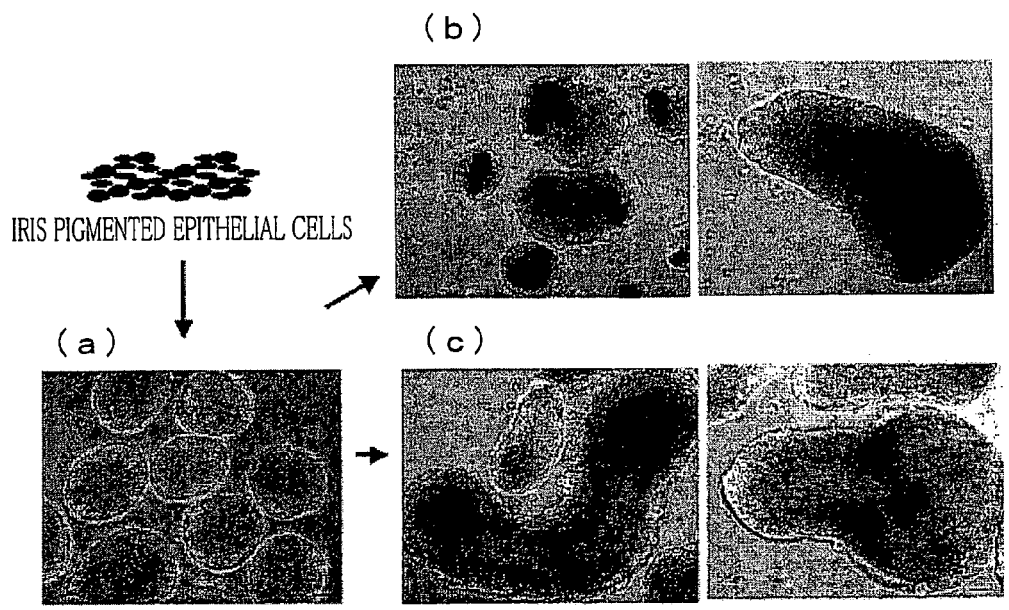
FIG. 3(a)   FIG. 3(b)
 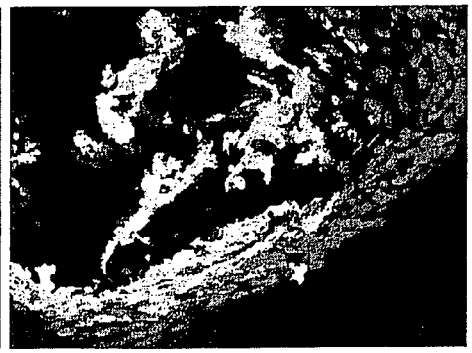

11-DAY-OLD RAT

Oct-3/4

DAPI

3-WEEK-OLD RAT

Oct-3/4

DAPI

METHOD FOR PRODUCING TISSUE CELLS FROM PLURIPOTENT STEM CELLS DERIVED FROM IRIS PIGMENT EPITHELIAL CELLS OF ANIMAL AND TISSUE CELL OBTAINED BY METHOD

TECHNICAL FIELD

The present invention relates to a method for producing tissue cells from pluripotent stem cells produced from iris pigmented epithelial cells of an animal. The present invention also relates to tissue cells obtained by the method.

BACKGROUND ART

Recently, attention has been paid to such regenerative medical treatment that transplants cells built by using pluripotency of brain- or spine-derived neural stem cells or that of ES cells (embryonic stem cells).

Medical applications of the neural stem cells and the ES cells raise many problems such as immunological rejection in cell transplantation, ethical issues, and unbalance between demand and supply of transplant cell sources.

Accordingly, when it becomes possible to use, as a transplant source, cells derived from a transplant recipient per se, autotransplantation becomes possible, thus solving the foregoing problems.

An example of cells expected to serve as the transplant sources is iris pigmented epithelial cells of an eyeball.

Iris pigmented epithelial cells are a component of an iris serving as tissue for opening and narrowing a pupil in accordance with an amount of light so as to adjust an amount of light which reaches a retina.

The inventors of the present invention have reported in Non-Patent Document 1 (Experimental Cell Res. (1998) 245, 245-251) that the inventors have successfully isolated and cultured iris pigmented epithelial cells of a chick.

Furthermore, the inventors have made it possible to isolate and culture mammalian iris cells (from mouse, rat, or human embryo) by a method improved from the process of Non-Patent Document 1 (see Non-Patent Document 2: Nature Neuroscience (2001) 4 (12), 1163).

It is possible to collect part of iris pigmented epithelial cells from a patient per se. Therefore, if it becomes possible to produce tissue cells by using iris pigmented epithelial cells, regenerative medical treatment using cells of the patient per se will be realized. (To the best of the inventors' search, there is no document concerning a method according to the present invention for producing tissue cells from stem cells derived from iris pigmented epithelial cells of an animal, and tissue cells obtained by the method.)

However, no method for producing non-neural cells from iris pigmented epithelial cells of an animal has been established.

The present invention has been completed in consideration of the foregoing problems and has an object to provide a method for producing tissue cells derived from iris pigmented epithelial cells of an animal, and tissue cells obtained by the method, the method and the tissue cells making it possible to solve problems such as immunological rejection in cell transplantation, ethical issues, and unbalance between the demand and supply of transplant cell sources.

DISCLOSURE OF INVENTION

As a result of diligently studying to attain the object, the inventors have found that an aggregate is obtained by culturing stem cells under specific culture conditions, the stem cells being obtained by using a floated coagulated mass culturing technique to selectively culture iris pigmented epithelial cells isolated from an eyeball of an animal. Further, the inventors have also found that the aggregate has an embryoid body structure which contains various tissue cells such as muscle cells, vascular endothelial cells, and other cells. Based on these findings, the inventors have completed the present invention. That is, the inventors have found that the stem cells are pluripotent stem cells differentiable into various types of tissue, the stem cells being obtained by selectively culturing the iris pigmented epithelial cells by using the floated coagulated mass culturing technique, the iris pigmented epithelial cells being isolated from the eyeball of the animal.

In order to attain the foregoing object, a method of the present invention for producing tissue cells includes the steps of: obtaining pluripotent stem cells by selectively culturing iris pigmented epithelial cells by a floated coagulated mass culturing technique, the iris pigmented epithelial cells isolated from an eyeball of an animal; and obtaining tissue cells from the pluripotent stem cells by culturing the pluripotent stem cells.

According to the foregoing arrangement, pluripotent stem cells can be obtained by selectively culturing an iris pigmented epithelium by using the floated coagulated mass culturing technique, the iris pigmented epithelium being isolated from iris tissue extirpated from an eyeball of an animal by using a publicly known conventional method for isolating an iris pigmented epithelium of an adult animal.

Moreover, by culturing the pluripotent stem cells, an embryoid body structure can be formed.

The embryoid body is a structure which contains tissue like an embryo, the tissue being made mainly from ES cells subjected to differentiation induction. Since the embryoid body contains tridermic cells, the iris-derived stem cells are believed to have totipotency like ES cells. Accordingly, in the present invention, the cells contained in the embryoid body structure derived from iris epithelial cells are referred to as "tissue cells derived from iris pigmented epithelial cells of an animal".

Pluripotent stem cells obtained during production of the tissue cells according to the present invention have an advantage of being collected and produced from autologous tissue relatively easily and in a low invasive manner. That is, unlike ES cells' conventionally used, the pluripotent stem cells do not have problems such as immunological rejection and ethical issues to which the use of ES cells face because ES cells are derived from a fetal embryo. Further, unlike pluripotent adult progenitor/stem cells (MAPC), the pluripotent stem cells do not require a highly invasive collection method such as bone marrow puncture.

In the present invention, the animal is for example a chicken, a mouse, a rat, or a human. Further, the animal may be a fetal individual or a postnatal individual. What is meant by the postnatal individual is an individual except for a prenatal embryo. As the postnatal individual, a sexually matured adult, a neonatal individual, and the like are exemplified. However, an individual may be of any age.

Further, the pluripotent stem cells have at least either one of the following characteristics (1) and (2).

(1) Oct-3/4 positive.
(2) tridermic differentiable.

The characteristics (1) and (2) will be described in Examples.

Further, the method of the present invention for producing tissue cells is arranged so that, in the step of obtaining the tissue cells from the pluripotent stem cells, the pluripotent stem cells are differentiated into one or more types of tissue cells by culturing the pluripotent stem cells under differentiation inducing condition.

Here, what is meant by "culturing under the differentiation inducing condition" is culturing under any publicly known conventional condition designed to differentiate cells. Specifically, it means a culturing method by which culturing is conducted in a medium, to which serum and a growth factor (e.g., FGF, EGF, CNTF, RA) is added, on a culture dish coated with various extracellular substrate components. Thus, the pluripotent stem cells are differentiable into one or more types of tissue cells by being cultured under the differentiation inducing condition.

It is preferable that the culturing under differentiation inducing condition be conducted with use of a serum. The serum is for example a fetal calf serum or an avian serum.

Further, in the culturing under the differentiation inducing condition, a growth factor may be further used. As the growth factor, for example, EGF (epidermal growth factor), FGF (fibroblast growth factor), and the like can be used.

The tissue cells according to the present invention are derived from iris pigmented epithelial cells part of which can be collected from a patient per se. Therefore, according to the present invention, the tissue cells which can be utilized as a transplant source in regenerative medical treatment can be produced from iris pigmented epithelial cells of an animal.

Further, the method of the present invention for producing tissue cells is arranged so that the isolating of the iris pigmented epithelial cells includes: an iris-tissue-extirpating step of extirpating iris tissue from the eyeball of the animal; and an iris-pigmented-epithelial-cell-separating step of separating iris pigmented epithelium from the iris tissue thus extirpated.

According to this arrangement, the tissue cells of the present invention can be efficiently produced by efficiently separating the iris pigmented epithelial cells of the animal.

Further, in the present invention, the iris-tissue-extirpating step includes: an iris-tissue-excising stage of excising only iris tissue from the eyeball of the animal; an enzyme treatment stage of subjecting the excised iris tissue to enzyme treatment; and an iris-tissue-restoring stage of restoring the enzyme-treated iris tissue.

According to this arrangement, the tissue cells of the present invention can be efficiently produced by efficiently extirpating only the iris tissue from the eyeball of the animal.

The tissue cells according to the present invention are obtained by using a method of the present invention for producing the tissue cells. As described above, the tissue cells are derived from iris pigmented epithelial cells of an animal. Therefore, the tissue cells of the present invention can be provided as a transplant cell source which solves problems such as immunological rejection caused by cell transplantation, ethical issues, and unbalance between the demand and supply of transplant cell sources.

Moreover, the tissue cells according to the present invention are ectodermal cells or cells derived from ectoderm, mesodermal cells or cells derived from mesoderm, or endodermal cells or cells derived from endoderm. Furthermore, the tissue cells of the present invention form tissue forming an intravital organ. The "tissue forming an intravital organ" specifically means nerve tissue, muscular tissue, heart tissue, vascular tissue, and the like which form a neural organ, a muscular organ, a heart, a blood vessel, and the like, respectively.

For a fuller understanding of the nature and advantages of the invention, reference should be made to the ensuing detailed description taken in conjunction with the accompanying drawings.

BRIEF DESCRIPTION OF DRAWINGS

FIG. 2A is a schematic drawing and FIGS. 2B-E are diagrams illustrating states of stem cells according to Example 1.

FIG. 3(A) and FIG. 3(B) are diagrams illustrating aggregates labeled with desmin (muscle cell marker) antibody or DAPI staining (nucleus) in Example 1.

BEST MODE FOR CARRYING OUT THE INVENTION

One embodiment of the present invention will be described below with reference to FIG. 1. The present invention is not to be limited to the embodiment.

For the purpose of solving problems such as immunological rejection in cell transplantation, ethical issues, and unbalance between the demand and supply of transplant cell sources, the inventors produced tissue cells derived from iris pigmented epithelial cells of an animal.

A method according to the present embodiment for producing tissue cells includes the steps of: obtaining pluripotent stem cells by selectively culturing iris pigmented epithelial cells by a floated coagulated mass culturing technique, the iris pigmented epithelial cells being isolated from an eyeball of an animal; and obtaining tissue cells from the pluripotent stem cells by culturing the pluripotent stem cells.

Figure 1:
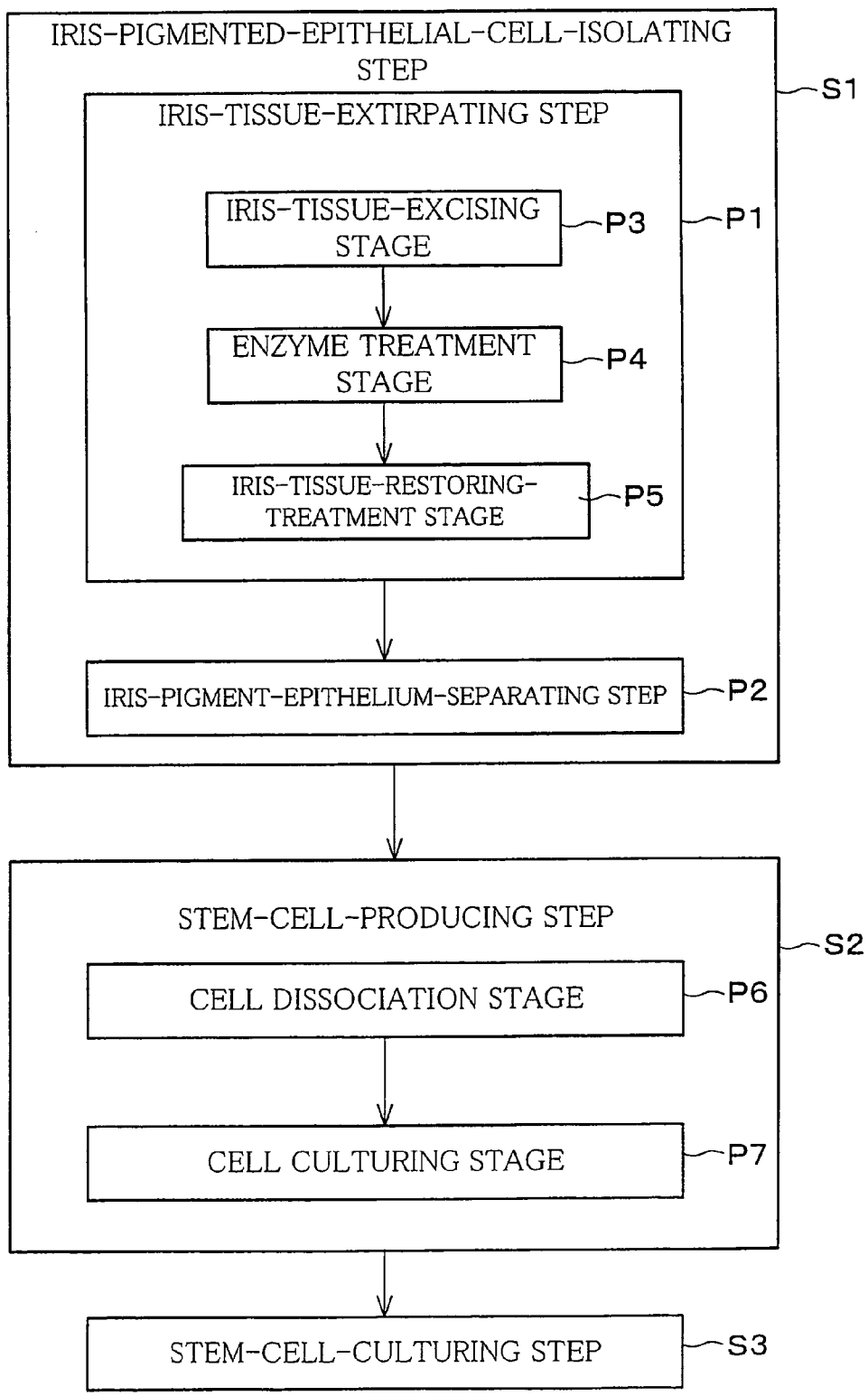
FIG. 1 is a schematic flow chart illustrating an example of a method according to the present invention for producing tissue cells.

That is, as shown in FIG. 1, the method of the present embodiment for producing tissue cells at least includes: iris-pigmented-epithelial-cell-isolating step (Step 1, hereinafter, Step is abbreviated as S) of isolating iris pigmented epithelial cells from an eyeball of an animal; the step of obtaining pluripotent stem cells by using the floated coagulated mass culturing technique to selectively culture the isolated iris pigmented epithelial cells (hereinafter, this step is referred to as stem-cell-producing step S2); and a step of obtaining tissue cells from the pluripotent stem cells by culturing the pluripotent stem cells with serum or the like (hereinafter, this step is referred to as stem-cell-culturing step S3). The method according to the present invention for producing a tissue cells is not limited to the above arrangement and may include another step. Further, the stem-cell-culturing step S3 can be referred to also as tissue-cell-inducing step.

The animal may be a postnatal individual animal of any age between a neonatal period and an adult period. That is, the method according to the present invention for producing tissue cells makes it possible to produce tissue cells derived from iris pigmented epithelial cells of an adult animal as well as tissue cells derived from iris pigmented epithelial cells of a neonatal animal.

The iris-pigmented-epithelial-cell-isolating step S1 is not particularly limited in terms of techniques and other features concretely adopted therein, as long as the iris pigmented epithelial cells can be obtained by the iris-pigmented-epithelial-cell-isolating step S1. Generally speaking, a publicly known conventional technique may be adopted so as to extirpate iris tissue from an eyeball of an animal and isolate iris pigmented epithelial cells from the extirpated iris tissue. It is preferable to use a method described in *Nature Neuroscience* (2001) 4 (12), 1163 (Non-Patent Document 2) so as to extirpate iris tissue from an eyeball of an animal.

In the stem-cell-producing step S2, it is only necessary to selectively culture only iris pigmented epithelial cells isolated from an eyeball of an animal. A specific technique and the like used in the step are not particularly limited. Generally speaking, it is only necessary to use a publicly known conventional technique so as to selectively culture only iris pigmented epithelial cells isolated from an eyeball of an animal.

Here, the stem-cell-producing step S2 includes Process 6 and Process 7 (hereinafter, Process is abbreviated as P). P6 is a cell dissociation stage at which iris pigmented epithelial cells, isolated in the iris-pigmented-epithelial-cell-isolating step S1, is dissociated from an aggregating state into an individual cell. P7 is a cell culturing stage at which only the isolated iris pigmented epithelial cells are selectively cultured.

In the following, the stages P6 and P7 of the stem-cell-producing step S2 will be described in detail. First, at the cell dissociation stage P6, the isolated iris pigmented epithelium cells arranged in a sheet-like form are dissociated into individual cells.

For example, at the cell dissociation stage P6, a commercially available trypsin solution is used to dissociate into the individual cells the isolated iris pigmented epithelium cells arranged in the sheet-like form. Further, for example, at the cell dissociation stage P6, the isolated iris pigmented epithelium cells arranged in the sheet-like form can be dissociated into the individual cells also by pipetting operation using a commercially available micropipette, without using the trypsin solution.

The reagent and instrument used at the cell dissociation stage P6 are not particularly limited, and it is possible to use a publicly known conventional reagent and instrument which make it possible to dissociate into individual cells the isolated iris pigmented epithelial cells in the coagulated state.

At the cell culturing stage P7, the isolated iris pigmented epithelial cells are cultured, in suspension, in a serum-free medium to which FGF (fibroblast growth factor), LIF (leukemia inhibitory factor), and SCF (human SCF (stem cell factor)) are added either individually or in combination. This allows the iris pigmented epithelial cells to grow without differentiation. This growth of the iris pigmented epithelial cells without differentiation leads to production of the tissue cells in higher quantity. This stage is preferably arranged to employ the floated coagulated mass culturing technique (neurosphere method), described in *Science* 1992: 225; 1707-1710, so as to selectively culture the iris pigmented epithelial cells isolated from the eyeball of the animal.

For example, at the cell culturing stage P7, a mixture of a commercially available serum-free medium and a commercially available N2 supplement is used as a floated-coagulated-mass-culturing culture medium. The iris pigmented epithelial cells dissociated at the cell dissociation stage P6 are cultured in the floated-coagulated-mass-culturing culture medium with rotating by use of a commercially available shaker. This makes it possible to selectively separate and collect a cell population which contains a large number of pluripotent stem cells.

The culture medium and reagent used at the cell culturing stage P7 are not particularly limited, and it is possible to use a publicly known conventional culture medium and reagent which make it possible to obtain the stem cells.

Further, in the present embodiment, a culture period in the cell culturing stage P7 may be set appropriately according to need. However, if the culture period is too long, the resulting aggregate may become overgrown thereby to be differentiated. Accordingly, in the present embodiment, it is preferable to carry out dissociation and passage of cells within three to four days.

Moreover, in the stem-cell-culturing step S3, the stem cells obtained at the cell culturing stage P7 are cultured with serum. The stem-cell-culturing step S3 is not particularly limited in terms of techniques and other features concretely adopted therein, as long as serum is used to culture the stem cells. Generally speaking, a publicly known conventional technique may be employed to culture the stem cells. Therefore, for example, the culturing of the stem cells may be carried out by using a commercially available micropipette to transfer the stem cells to a serum-containing medium.

As the serum, a fetal calf serum, an avian serum, and the other serums can be exemplified. However, the serum is not to be limited to these. Further, in the present embodiment, these serums may be used solely or two or more of these serums may be used according to need.

Further, a concentration of the serum is preferably 5 to 30% and more preferably 10 to 20%. When the culture is conducted at such a serum concentration, a good result is obtained. However, the present invention can be conducted at a concentration lower or higher than that. Therefore, the serum concentration is not limited as described above.

In the present embodiment, the stem cells may be cultured with a growth factor in addition to the serum. Specifically, as the growth factor, EGF (epidermal growth factor), FGF (fibroblast growth factor), and the other growth factor can be exemplified. In the present embodiment, these growth factors may be used solely or two or more of these growth factors may be used according to need.

Further, a concentration of the growth factor is not particularly limited and may be set appropriately according to need.

Further, in the present embodiment, in the stem-cell-culturing step S3, a culture period to culture the stem cells is preferably one to three months, albeit not particularly limited. In the stem-cell-culturing step S3, when a culture period is one month or shorter (particularly, two weeks or shorter), differentiation induction efficiency undesirably decreases. Conversely, when a culture period is three months or longer, a cell survival rate within the aggregates may undesirably decrease.

In the present embodiment, an embryoid body is obtained by conducting the stem-cell-culturing step S3. The embryoid body is derived from the iris pigmented epithelial cells of the animal, and the iris pigmented epithelial cells are ectodermal cells. Therefore, the embryoid body obtained in the present embodiment encompasses not only neural stem cells but also various tissue cells such as muscular cells and vascular endothelial cells. Thus, according to the present embodiment, the tissue cells derived from the iris pigmented epithelial cells of an animal can be obtained by conducting the stem-cell-culturing step S3.

The method according to the present embodiment for producing tissue cells is arranged so that the isolating of the iris pigmented epithelial cells includes: an iris-tissue-extirpating step of extirpating iris tissue from the eyeball of the animal; and an iris-pigmented-epithelial-cell-separating step of separating an iris pigmented epithelium from the iris tissue thus extirpated. Note that the method of the present embodiment for producing tissue is not to be limited to this arrangement by may include another step.

That is, as illustrated in FIG. 1, the method of the present embodiment for producing tissue cells includes at least the iris-pigmented-epithelial-cell-isolating step S1, the stem-cell-producing step S2, and the stem-cell-culturing step S3. Furthermore, the iris-pigmented-epithelial-cell-isolating step S1 includes an iris-tissue-extirpation step P1 and an iris-pigmented-epithelial-cell-separating step P2. The method according to the present embodiment for producing the tissue cells is not limited to this arrangement and may include another step.

The iris-tissue-extirpating step P1 is not particularly limited in terms of technique and the like concretely adopted, as long as the iris tissue can be extirpated from the eyeball of the animal. Generally speaking, a publicly known conventional technique may be used so as to extirpate the iris tissue from the eyeball of the animal it is referable to use the method described in *Nature Neuroscience* (2001) 4 (12), 1163 (Non-Patent Document 2), so as to extirpate the iris tissue from the eyeball of the animal.

Here, as shown in FIG. 1, the iris-tissue-extirpation step P1 includes: an iris-tissue-excising stage P3 of excising only the iris tissue from the eyeball of the animal; an enzyme treatment stage P4 of subjecting the extirpated iris tissue to an enzyme treatment; and an iris-tissue-restoring-treatment stage P5 of restoring the enzyme-treated iris tissue. The method according to the present embodiment for producing the tissue cells is not limited to this arrangement and may include another step.

In the following, each of the stages P3 to P5 of the iris-tissue-extirpating step P1 will be described in detail. First, the iris-tissue-excising stage P3 is not particularly limited in terms of technique and the like concretely adopted, as long as the iris tissue can be extirpated from the eyeball of the animal. Generally speaking, a publicly known conventional technique may be used so as to excise only the iris tissue from the eyeball of the animal.

For example, at the iris-tissue-excising stage P3, commercially available micro scissors are used to excise only iris tissue from an eyeball of an animal.

The enzyme treatment stage P4 is designed to subject the iris tissue to the enzyme treatment in order to make it easy to separate an iris pigmented epithelium from the iris tissue. The enzyme treatment stage P4 is not particularly limited in terms of technique and the like concretely adopted. Generally speaking, a publicly known conventional technique may be used to subject the iris tissue to the enzyme treatment in order to make it easy to separate the iris pigmented epithelium from the iris tissue.

For example, in case of separating an iris pigmented epithelium from an eyeball of a chicken, at the enzyme treatment stage P4, iris tissue is allowed to react for 15 to 40 minutes in a dispase solution containing a commercially available dispase. Thereafter, the iris tissue is allowed to react for 20 to 30 minutes in an EDTA solution containing a commercially available EDTA (ethylenediaminetetraacetic acid). The enzyme and reagent used at the enzyme treatment stage P4 are not particularly limited. It is possible to use a publicly known conventional enzyme and reagent which make it possible to treat iris tissue in such a way as to make it easy to separate the iris pigmented epithelium from the iris tissue.

The iris-tissue-restoring-treatment stage P5 is designed to restore the iris tissue weakened by enzyme treatment. The iris-tissue-restoring-treatment stage P5 is not particularly limited in terms of technique and the like concretely adopted. Generally speaking, a publicly known conventional technique may be used so as to restore the iris tissue weakened by enzyme treatment.

For example, at the iris-tissue-restoring stage P5, after the reaction of the enzyme treatment stage P4, the iris tissue is allowed to react for 30 to 60 minutes in a culture medium containing a commercially available fetal calf serum so as to restore the iris tissue. The serum-containing culture medium and reagent used at the iris-tissue-restoring-treatment stage P5 are not particularly limited. It is possible to use a publicly known conventional culture medium and reagent which make it possible to recover weakened iris tissue.

Further, in the iris-tissue-extirpating step P1, the reaction times at the enzyme treatment stage P4 and the reaction time at the iris-tissue-restoring-treatment stage P5 are particularly important. By adjusting the reaction time during which the iris tissue is allowed to react in the dispase solution at the enzyme treatment stage P4, the reaction time during which the iris tissue is allowed to react in the EDTA solution at the enzyme treatment stage P4, and the reaction time during which the iris tissue is allowed to react in the fetal-calf-serum-containing culture medium at the iris-tissue-restoring-treatment stage P5, it is possible to separate an iris pigmented epithelium not only from the eyeball of the chicken but also from an eyeball of an animal such as a mouse, a rat, or a human being.

In case of separating the iris pigmented epithelium from the eyeball of the mouse, it is preferable that the iris tissue be allowed to react in 1000 U/mL dispase solution at 25 to 37° C. for 15 to 40 minutes, then in 0.05 to 0.1% EDTA solution at room temperature for 16 to 40 minutes, and then in a culture medium with 8 to 10% fetal calf serum content at room temperature for 30 to 120 minutes.

Further, in case of separating an iris pigmented epithelium from an eyeball of a ten-day-old mouse, it is particularly preferable that the iris tissue be allowed to react in 1000 U/mL dispase solution at 37° C. for 16 minutes, then in 0.05% EDTA solution at room temperature for 20 minutes, and then in a culture medium with 8% fetal calf serum content at room temperature for 90 minutes.

Further, in case of separating an iris pigmented epithelium from an eyeball of a twelve-day-old mouse, it is particularly preferable that the iris tissue be allowed to react in 1000 U/mL dispase solution at 37° C. for 20 minutes, then in 0.05% EDTA solution at room temperature for 25 minutes, and then in a culture medium with 8% fetal calf serum content at room temperature for 60 minutes.

Further, in case of separating an iris pigmented epithelium from an eyeball of a two-month-old mouse, it is particularly preferable that the iris tissue be allowed to react in 1000 U/mL dispase solution at 37° C. for 30 minutes, then in 0.05% EDTA solution at room temperature for 40 minutes, and then in a culture medium with 8% fetal calf serum content at room temperature for 30 minutes.

In case of separating an iris pigmented epithelium from an eyeball of a rat, it is preferable that the iris tissue be allowed to react in 1000 U/mL dispase solution at 37° C. for 15 to 40 minutes, then in 0.05 EDTA solution at room temperature for 15 to 60 minutes, and then in a culture medium with 8 to 10%. fetal calf serum content at room temperature for 30 to 120 minutes.

In case of separating an iris pigmented epithelium from an eyeball of a human embryo, it is preferable that the iris tissue be allowed to react in 500 to 1000 U/mL dispase solution at 25 to 37° C. for 15 to 30 minutes, then in 0.05 to 0.1% EDTA solution at room temperature for 15 to 40 minutes, and then in a culture medium with 8 to 10% fetal calf serum content at room temperature for 10 to 60 minutes.

Further, in case of separating an iris pigmented epithelium from an eyeball of a nineteen-week-old human after birth, it is particularly preferable that the iris tissue be allowed to react in 1000 U/mL dispase solution at 37° C. for 30 minutes, then in 0.05% EDTA solution at room temperature for 30 minutes, and then in a culture medium with 8% fetal calf serum content at room temperature for 60 minutes.

As the culture medium, for example, a DMEM medium (manufactured by Invitrogen Corporation) with a commercially available fetal calf serum of an appropriate amount can be used.

The iris-pigmented-epithelium-separating step P2 is not particularly limited in terms of technique an the like concretely adopted, as long as the iris pigmented epithelium can be separated from the iris tissue extirpated in the iris-tissue-extirpating step P1, the iris tissue including iris stroma and the iris pigmented epithelium. Generally speaking, a publicly known conventional technique may be used so as to separate only the iris pigmented epithelium from the iris tissue.

For example, the iris-pigmented-epithelium-separating step P2 may be arranged so that the iris stroma and the iris pigmented epithelium are separated by peeling and collecting the iris pigmented epithelium from the restored iris tissue by using commercially available micro forceps.

Thus, according to the present embodiment, the iris pigmented epithelial cells are isolated by the iris-tissue-extirpating step P1 and the iris-pigmented-epithelium-separating step P2. This allows efficient separation of the iris pigmented epithelial cells, thereby making it possible to efficiently produce the tissue cells.

As described above, the tissue cells according to the present invention are derived from iris pigmented epithelial cells part of which can be collected from a patient per se. Therefore, according to the present embodiment, pluripotent stem cells differentiable into various tissue cells can be produced from the iris pigmented epithelial cells of the patient per se. Moreover, by culturing the pluripotent stem cells under various differentiation inducing conditions, various tissue cells can be further produced which can be utilized as transplant sources in regenerative medical treatment. Further, use of the tissue cells of the present embodiment as a transplant cell source can solve problems such as immunological rejection in cell transplantation, ethical issue, and unbalance between the demand and supply of transplant source cells.

EXAMPLES

In the following, the present invention will be described more specifically with reference to examples and FIGS. 2 to 6(b). The examples are not to limit the present invention.

Example 1

(Isolation of Iris Pigmented Epithelial Cells)
Only iris tissue was excised from an eyeball of a chick by using commercially available micro scissors. The iris tissue was allowed to react in 1000 U/mL of a dispase solution ("dispase"; manufactured by Godo Seishu Co., Ltd.) for 15 to 40 minutes at 37° C. Thereafter, the iris tissue was allowed to react in 0.05% EDTA (ethylenediaminetetraacetic acid) solution for 20 to 30 minutes at room temperature.

After the reaction, the iris tissue was allowed to react for 30 to 60 minutes in a culture medium ("DMEM medium"; manufactured by Invitrogen Corporation) with 8% fetal calf serum content, thereby to restore the iris tissue. Thereafter, by peeling and collecting only iris pigmented epithelium from the iris tissue by using commercially available micro forceps, the iris pigmented epithelium was separated from iris matrix.

(Floated Coagulated Mass Culturing Technique)
The separated iris pigmented epithelium was dissociated into cells by using a commercially available trypsin solution. Thereafter, the dissociated iris pigmented epithelial cells were selectively cultured according to the floated coagulated mass culturing technique (neurosphere method) described in *Science* 1992: 225; 1707-1710.

Used as a floated-coagulated-mass-culturing medium was a serum-free medium ("DMEM/F12 medium"; manufactured by Invitrogen Corporation) either with the addition of a 1/100 volume of an N2 supplement (manufactured by Invitrogen Corporation) and 20 ng/mL of an FGF2 (fibroblast growth factor-2; manufactured by PeproTech Inc.), or with the addition of a 1/100 volume of an N2 supplement (manufactured by Invitrogen Corporation), 1000 U/mL of an LIF (leukemia inhibitory factor, ESGRO; manufactured by CHEMICON International, Inc.), and 10 ng/mL of an SCF (human SCF (stem cell factor); manufactured by DIA-CLONE).

With rotating by a commercially available shaker, the trypsin-treated iris pigmented epithelial cells were cultured in the floated-coagulated-mass-culturing medium in a $CO_2$ incubator for three to seven days In this way, stem cells were obtained The obtained stem cells are illustrated in FIG. 2(A).

(Formation of an Aggregate by Stem Cell Culturing)
After the iris pigmented epithelial cells insolated from the eyeball of the chick had been subjected to the floated coagulated mass culturing, the stem cell culturing was conducted as follows.

The stem cells, derived from the iris pigmented epithelial cells of the chick and obtained by the floated coagulated mass culturing technique, were transferred to each of the following medium (b) and (c), by using a commercially available micropipette.

(b) a DMEM medium (manufactured by Invitrogen Corporation) containing fetal calf serum (8%) and avian serum (2%).

(c) a DMEM medium (manufactured by Invitrogen Corporation) containing fetal calf serum (8%) and growth factors EGF and FGF2 (20 ng/mL each).

Moreover, the stem cells were cultured for 1 to 2 months by respectively using the media (b) and (c) As a result, aggregates as illustrated in FIGS. 2B-C and FIGS. 2D-E, respectively, were obtained.

The aggregates obtained by culturing the stem cells in the medium (b) and (c) were labeled using desmin antibody (muscular cell marker) and DAPI staining (nucleus). The results are illustrated in FIGS. 3(A) and 3(B). FIG. 3(A) illustrates aggregates obtained by culturing the stem cells in medium (b) FIGS 2B and 2C) FIG. 3(B) illustrates aggregates obtained by culturing the stem cells in medium (c) (FIGS. 2D and 2E). In FIGS. 3(A) and 3(B), the white part indicates an image of the aggregates labeled with desmin, and the gray part indicates an image of the aggregates labeled by DAPI staining (nucleus).

Example 2

Iris pigmented epithelial cells were dissociated in the same manner as in Example 1. The iris pigmented epithelial cells were cultured for three days in a serum-free medium ("DMEM/F12 medium"; manufactured by Invitrogen Corporation), with a 1/100 volume of an N2 supplement (manufactured by Invitrogen Corporation), and 20 ng/mL of FGF2 (fibroblast growth factor-2p; manufactured by PeproTech Inc.). Thereafter, the iris pigmented epithelial cells were cultured for one to two months according to the floated coagulated mass culturing technique in three types of medium having the following compositions (1) to (3).
(1) Fetal calf serum (8%), EGF (20 ng/mL), and FGF2 (20 ng/mL).
(2) Fetal calf serum (8%) and avian serum (2%).
(3) Fetal calf serum (8%), avian serum (2%), EGF (20 ng/mL), and FGF2 (20 ng/mL).

RNA was extracted from the obtained aggregates. RT-PCR technique was used to examine absence and presence of gene expression of the followings: fetoprotein a, which is an endodermal marker; myosin and MEF2, which are mesodermal markers; and pax 6 and tubulin J, which are ectodermal markers. As a result, under any one of conditions (1) to (3), expression of the marker genes was observed. This shows that the obtained aggregates include cells differentiated into all the three types of tridermic tissue.

The result showed that the aggregates have a similar property to that of a cell structure called an embryoid body which is formed mainly from ES cells by differentiation induction and which contains various differentiated cells like an embryo does. Although the iris pigmented epithelial cells are ectodermal cells, the present example showed that it is possible to allow stem cells derived from iris pigmented epithelial cells of an animal to be differentiated into mesodermal cells and endodermal cells as well as ectodermal cells. That is, the present embodiment showed that the cells obtained by the stem-cell-producing step have tridermic differentiation potency and can be differentiated into any one of a mesoderm, an endoderm, and an ectoderm.

Figure 4:
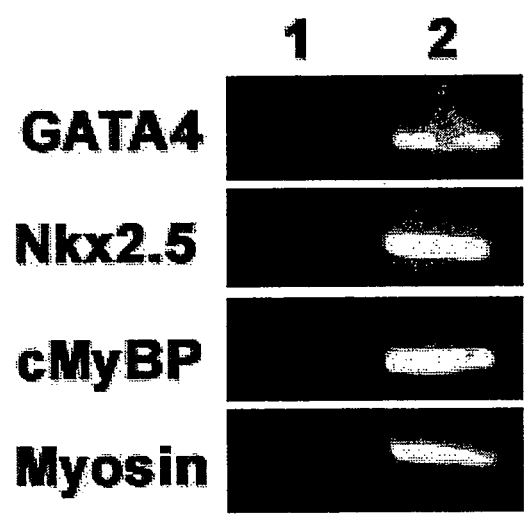
FIG. 4 is a diagram illustrating emergence of myocardial cells in each step of inducing each tissue cell from iris pigmented epithelial cells in Example 2.

Further, FIG. 4 illustrates results of PT-PCR to confirm expression induction of a gene specific for myocardial cells. RNA were extracted from the cultured cells obtained at the stage of culturing the cells on the serum-free media for three days (i.e., the stem-cell-producing step S2) and from the cultured cells obtained at the subsequent stage of culturing the cells for one to two months (i.e., the stem-cell-culturing step S3).

Lane 1 illustrates the result obtained from a sample taken on a second day of the culturing of the cell culturing stage S7 in the stem-cell-producing step S2. Further, Lane 2 illustrates a result obtained from a sample taken after two-month culturing under condition (3) in the stem-cell-culturing step S3. From the results, it was found that at the stem-cell-producing step (Lane 1) the pluripotent stem cells were yet to be differentiated into tissue cells, and in the stem-cell-culturing step (Lane 2), the pluripotent stem cells were differentiated into the myocardial cells.

Example 3

Figure 5:
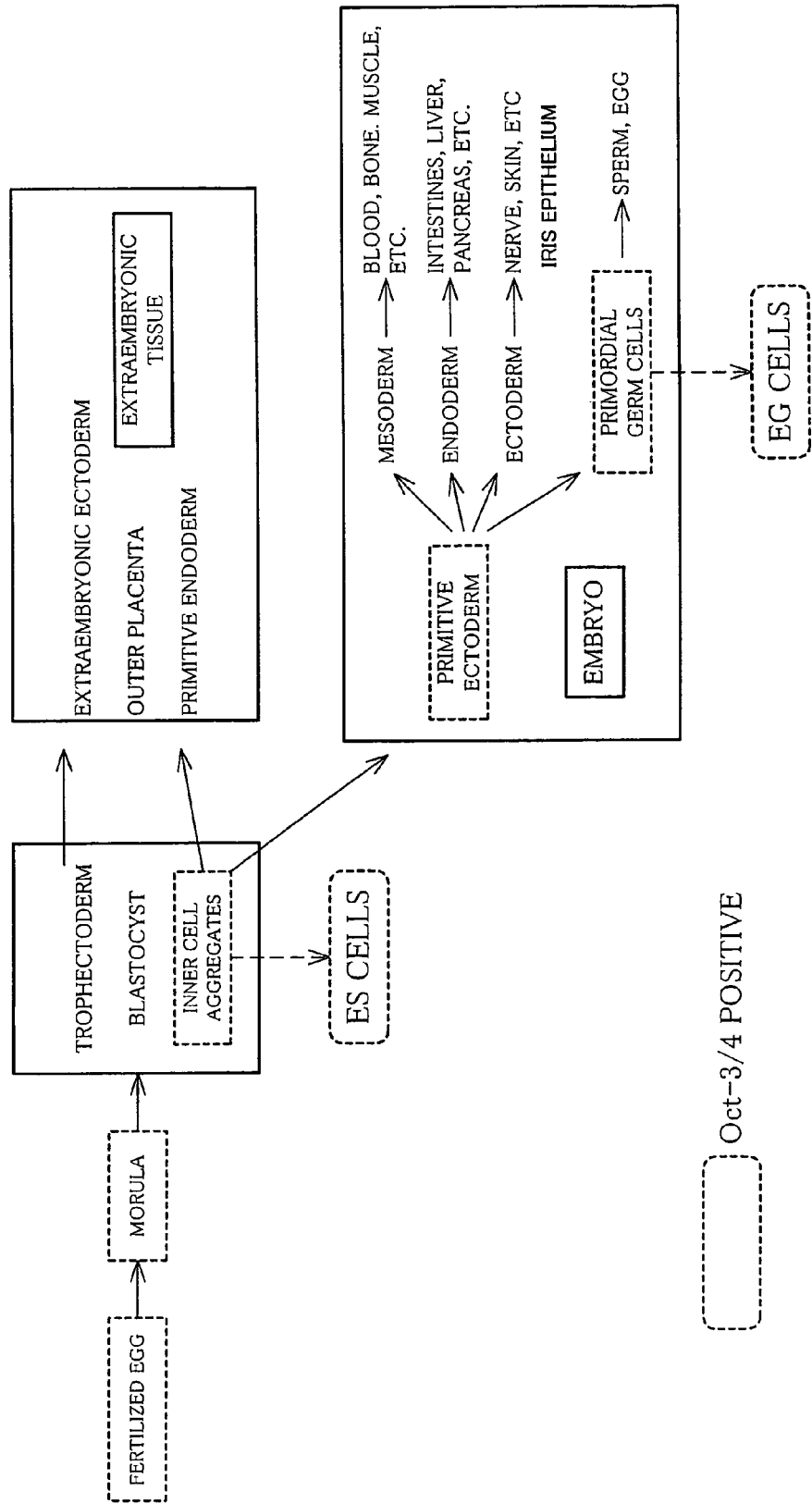
FIG. 5 is a diagram explaining an expression pattern of Oct-3/4 in an initial developmental process of a mouse.

Oct-3/4 is a molecule which is expressed specifically in undifferentiated totipotent cells, and quite limited kinds of cells show the presence of Oct-3/4 (see "system of expression of Oct-3/4 in early development of mouse" shown in FIG. 5). It is known that after birth Oct-3/4 is expressed only in spermatogenous cells which are reproductive stem cells. It is believed that Oct-3/4 is not expressed in another type of somatic cell tissue after birth.

Figure 6A:
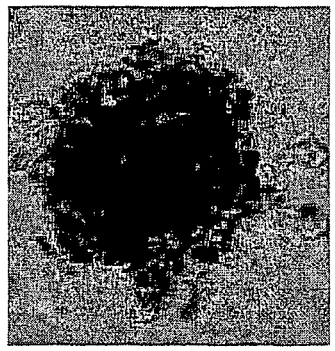
FIG. 6(A) is a diagram illustrating a result of labeling a rat-obtained stem cell by Oct-3/4 antibody staining and DAPI staining in Example 3.
Figure 6A:
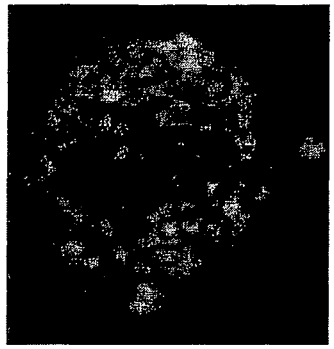
Figure 6A:
Figure 6B:
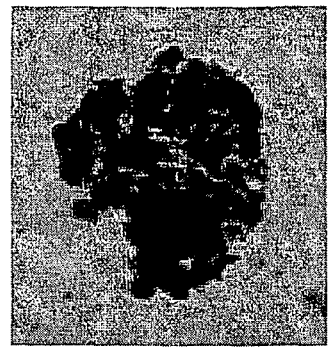
FIG. 6(B) is a diagram illustrating a result of labeling a rat-obtained stem cell by Oct-3/4 antibody staining and DAPI staining in Example 3.
Figure 6B:
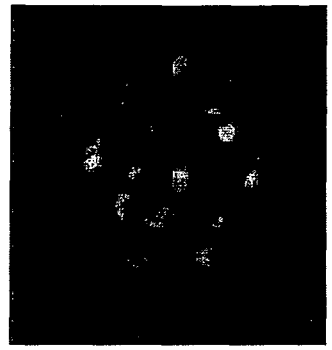
Figure 6B:
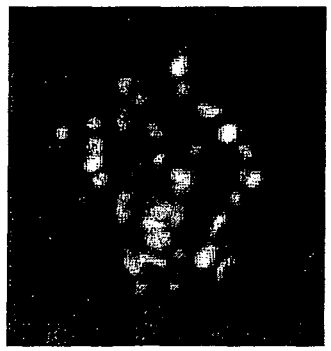

The present example examined expression of Oct-3/4 in iris tissue of a postnatal mouse and a postnatal rat and in parts of stem cells obtained from their iris tissue. The result is illustrated in FIGS. 6(A) and 6(B) FIG. 6(A) illustrates stem cells obtained from an eleven-day-old rat using the method according to the present invention and labeled by Oct-3/4 antibody staining and DAPI staining. The white color indicates the labeled portion. FIG. 6(B) illustrates stem cells obtained from a three-week-old rat using the method according to the present invention and labeled by Oct-3/4 antibody staining and DAPI staining. The white color indicates the labeled portion. From FIGS. 6(A) and 6(B), it can be understood that an Oct-3/4 gene and a gene product (Oct-3/4 protein) were expressed both in the iris tissue of the postnatal mouse and the postnatal rat and in the parts of the stem cells obtained from the iris tissue (i e they are all Oct-3/4 positive).

This result indicates that there is a high possibility that iris, which is somatic cell tissue, also contain cells which still has undifferentiated titopotency. If it becomes possible to purify and culture the cells and to induce differentiation of the purified and cultured cells under proper conditions, it will become possible to produce various tissue cells therefrom. Research of regenerative medical treatment involving application of ES cells is actively carried out, but it presents huge ethical issues. In case of iris tissue, it is possible to use cells of a patient per se. Therefore, it is expected that use of iris tissue will lead to realization of regenerative medical treatment using autotransplantation.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Industrial Applicability

As described above, according to a method of the present invention for producing tissue cells, pluripotent stem cells differentiable into various tissue cells are produced from iris pigmented epithelial cells of an animal, and various tissue cells can be produced from the pluripotent stem cells. The tissue cells can be used as a transplant source in regenerative medical treatment.

Further, tissue cells obtained by the producing method of the present invention can be provided as a transplant source, which solves problems such as immunological rejection in cell transplantation, ethical issues, and unbalance between the demand and supply of transplant source cells.

The invention claimed is:
1. A method for producing tissue cells wherein the tissue cells are myocardial cells, the method comprising the steps of:
(i) an iris-tissue-extirpating step of extirpating iris tissue from the eyeball of the animal;
(ii) an iris-pigmented-epithelial-cell-separating step of separating iris pigmented epithelium from the iris tissue thus extirpated;
(iii) dissociating the separated iris pigmented epithelium using a trypsin solution;
(iv) obtaining pluripotent stem cells by selectively culturing iris pigment epithelial cells by a floated coagulated mass culturing technique, the iris pigmented epithelial cells separated by the steps (i)-(iii) being isolated from an eyeball of an animal, the floated coagulated mass culturing technique comprising culturing the isolated iris pigmented epithelial cells in a culturing media with rotation, the culturing media comprising serum free medium, an N2 supplement, and at least one factor selected from the group consisting of fibroblast growth factor (FGF), leukemia inhibitory factor (LIF), and stem cell factor (SCF); and (v) obtaining myocardial cells from the pluripotent stem cells by differentiating the pluripotent stem cells into myocardial cells by culturing the pluripotent stem cells under differentiation-inducing conditions comprising culturing the pluripotent stem cells for one to two months in a culture medium comprising fetal calf serum, avian serum, epidermal growth factor (EGF), and fibroblast growth factor 2 (FGF2).

2. The method according to claim 1, wherein the animal is a chicken, a mouse, a rat, or a human.

3. The method according to claim 1, wherein the animal is a postnatal individual animal.

4. The method according to claim 1, wherein the pluripotent stem cells are Oct-3/4 positive and/ or tridermic differentiatable.

5. The method according to claim 1, wherein the iris-tissue-extirpating step includes:
   an iris-tissue-excising stage of excising only iris tissue from the eyeball of the animal;
   an enzyme treatment stage of subjecting the excised iris tissue to enzyme treatment; and
   an iris-tissue-restoring stage of restoring, by using a culture medium containing serum, the iris tissue weakened by the enzyme treatment.

6. The method according to claim 5, wherein in the enzyme treatment step, the iris tissue is treated in a dispase solution and then treated in an EDTA solution.

7. The method according to claim 5, wherein in the iris-restoring step, the iris tissue is treated in a culture medium comprising fetal calf serum.

8. The method of claim 1, further comprising testing for expression of at least one gene specific for myocardial cells.

9. The method of claim 8, wherein the gene specific for myocardial cells is selected from the group consisting of GATA4, Nkx2.5, cMyBP, and myosin.

10. The method of claim 1, further comprising examining the pluripotent stem cells, after step (iv), for absence or presence of expression of an endodermal marker gene, a mesodermal marker gene, and an ectodermal marker gene.

11. The method of claim 10, wherein the endodermal marker gene is fetoprotein α, the mesodermal marker gene is myosin or MEF2, and the ectodermal marker is pax 6 or tubulin J.

* * * * *